United States Patent [19]

Parshall et al.

[11] Patent Number: 4,507,241

[45] Date of Patent: Mar. 26, 1985

[54] METHOD FOR THE HYDROCARBYLATION OF NAPHTHOQUINONE DERIVATIVES

[75] Inventors: George W. Parshall; Wilson Tam, both of Wilmington, Del.

[73] Assignee: E. I. Du Pont de Nemours and Company, Wilmington, Del.

[21] Appl. No.: 472,753

[22] Filed: Mar. 7, 1983

[51] Int. Cl.$^3$ .............................................. C07C 50/12
[52] U.S. Cl. ........................... 260/396 R; 260/687 R; 260/429.7; 260/448 A; 260/429.3; 260/429.9
[58] Field of Search ........................... 260/396 R, 687

[56] References Cited

U.S. PATENT DOCUMENTS

| | | | |
|---|---|---|---|
| 4,049,705 | 9/1977 | Schwing | 260/512 C |
| 4,110,473 | 8/1978 | Fagitt et al. | 424/331 |
| 4,266,066 | 5/1981 | Spielmann et al. | 549/64 |

OTHER PUBLICATIONS

Swenton et al., *J. Am. Chem. Soc.*, 100, pp. 6182–6188 (1978).
Boehm et al., *J. Medicinal Chem.*, pp. 295–299 (1981).
Wailes, *Organometallic Chemistry of Titanium, Zirconium and Hafnium*, 1974, p. 168, Academic Press, N.Y., N.Y.
Grignard, Rections of Nonmetallic Substances, Kharesch, 1954, pp. 530, 531, 536 & 537, Prentice-Hall Inc., N.Y. N.Y.
Negishi et al., Tet. Letter, 3737 (1981).
Kobayashi et al., JOC, 45, 5223 (1980).
Milstein et al., JOC 44, 1613, 1979.
Houben-Weyl, Methoden der Organischen Chem, 7/3a, Chinone I, Vierte Auflage, pp. 23 to 112.

*Primary Examiner*—Glennon H. Hollrah
*Assistant Examiner*—Raymond K. Covington
*Attorney, Agent, or Firm*—James A. Costello

[57] ABSTRACT

A method for the hydrocarbylation of naphthoquinones comprising cross-coupling addition of the hydrocarbyl moiety of selected organometallic reagents to leaving group-substituted naphthoquinones.

15 Claims, No Drawings

METHOD FOR THE HYDROCARBYLATION OF NAPHTHOQUINONE DERIVATIVES

BACKGROUND OF THE INVENTION

This invention concerns a method for making naphthoquinone intermediates to known antimalarial and miticidal compounds.

Cross-coupling addition of organometallic reagents to certain organic halides, acetates, sulfonoxy compounds and the like is known. It is also known to catalyze such reactions, if necessary, with Ni(0) or Pd(0) complexes. However, it was not known heretofore that organometallic reagents can be cross-coupled to 1,4-naphthoquinones. Representative of the state of the art relative to cross-coupling addition reactions are the following.

Corriu et al., *JCS Chem. Comm.*, 144 (1972) and Kumada et al., *JACS*, 94, 4374 (1972) disclose the nickel-catalyzed cross-coupling of Grignard reagents with halides.

Oku Rado et al., *Tet. Letter*, 12, 1027 (1978) disclose Pd(0) catalyzed alkenylation of bromocyclohexenone:

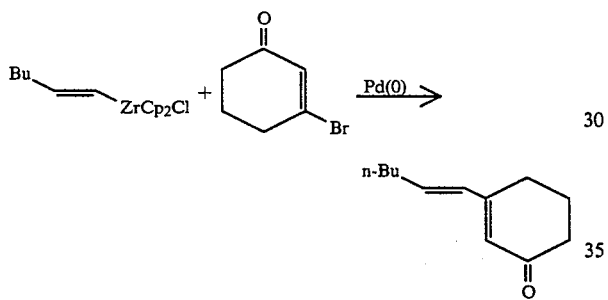

where the Pd(0) catalyst=PdCl$_2$(P$\phi_3$)$_2$+i-Bu$_2$AlH.

Negishi et al., *Tet. Letter*, 3737 (1981) disclose Pd(0) catalyzed coupling of alkenyl halides with allylic aluminum and phenyl zinc, aluminum and zirconium reagents.

Negishi et al., *JOC*, 45, 5223 (1980) disclose Pd(0)-catalyzed coupling of β-halo-α, β-unsaturated carbonyl derivatives with homoallylic zinc halides:

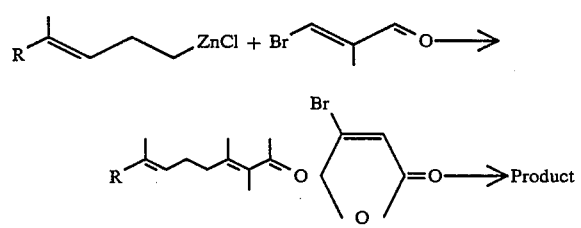

where the catalyst can be Pd(P$\phi_3$)$_4$ or PdCl$_2$(P$\phi_3$)$_2$+(i-Bu)$_2$AlH.

U.S. Pat. No. 4,266,066 discloses reaction of aluminum alkyls with acid chlorides to yield ketones, optionally in the presence of AlX$_3$ and in methylene chloride as solvent.

Stille, *JOC*, 44, 1613, 1979, reported reaction of acid chlorides with SnR$_4$ (R=alkyl) in the presence of Pd(0) catalysts to yield ketones. The reaction occurs in the presence of a variety of functional groups including aldehyde.

U.S. Pat. No. 4,049,705 discloses preparation of 2-n-dodecyl-3-chloronaphthoquinone by reaction of 2-dodecyl-1-naphthol with sulfuric acid to give sulfonic acid, followed by chlor-oxidation with FeCl$_3$/H$_2$SO$_4$.

Houben-Weyl, *Methoden der Organischen Chemie*, 7/3a, Chinone I, Vierte Auflage, pages 23 to 111 describes preparation of a variety of alkylnaphthoquinones.

U.S. Pat. No. 4,110,473 discloses preparation, from 2-alkyl-1-naphthol through 4-sulfonation, chlor-oxidation with chlorine and ferric chloride, and alkylation, of miticidal 2-alkoxy-3-alkyl-1,4-naphthoquinones.

U.S. Pat. No. 4,266,066 discloses reaction of acid chlorides with aluminum alkyls to yield ketones.

SUMMARY OF THE INVENTION

This invention concerns a method for the cross-coupling addition reaction of a leaving-group-substituted naphthoquinone with an organometallic reagent wherein the naphthoquinone reactant has the formula

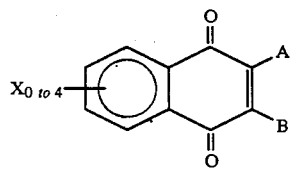

where:

A and B are the same or different and are selected from the group consisting essentially of H, C$_1$ to 3 alkyl, Cl, Br, I, —OR,

—OCR$^1$, and

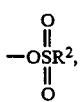
—OSR$^2$, provided that no more than one of A and B is H or C$_1$ to 3 alkyl;

X is hydrocarbyl of up to about 20 carbons, including straight, branched or cyclic alkyl, aryl, fused-ring aryl, aralkyl, or alkaryl;

R is C$_1$ to C$_5$ alkyl;

R$^1$ is C$_1$ to C$_5$ alkyl, C$_1$ to C$_5$ perfluoroalkyl, or aryl;

R$^2$ is aryl;

with an organometallic compound comprising (i) a metal from Group 2B, Group 3B, Group 4B, or the transition metal groups of the Periodic Table, and (ii) a hydrocarbyl organic moiety. See, F. A. Cotton and G. Wilkinson, "Advanced Inorganic Chemistry", Third Ed., 1972, Wiley Interscience, N.Y., for further details concerning the particular version of the Periodic Table employed herein.

Representative organometallic compounds are as follows:

R$^3_4$Sn where R$^3$ is C$_1$ to C$_{20}$ alkyl, cycloalkyl, aryl, or C$_7$ to C$_{20}$ aralkyl;

$R^4{}_n AlX_{3-n}$ where $R^4$ is $C_2$ to $C_{20}$ alkyl, cycloalkyl, aryl, $C_7$ to $C_{20}$ aralkyl, or $C_3$ to $C_{20}$ alkenyl; X is —Cl, —Br, —I, or $R^4$, and n=1, 2, or 3;

$Cp_2ZrXR^4$ where $R^4$ and X are as defined above, and Cp is the cyclopentadienyl ligand; and $R^4ZnX$ where $R^4$ and X are as defined above.

DETAILS OF THE INVENTION

It is contemplated that there can be from one to four substituents, X, on the left ring of the naphthoquinone. The number and location of said substituents is not particularly pertinent provided one avoids steric problems and competitive reactivity of such substituents with the organometallic reagent.

Representative of the leaving group substituents on the 1,4-naphthoquinone starting reactant are halogens and oxy-containing groups such as alkoxy, acyloxy, sulfonoxy and the like.

Catalysts, such as $NiCl_2(dppp)$, $PdCl_2(dppp)$, $Pd(PR^5{}_3)_4$, $PdX_2(PR^5{}_3)_2$, or $PdCl_2(CH_2\phi)(P\phi_3)_2$ (dppp represents $\phi_2P(CH_2)_3P\phi_2$ and $R^5$ represents alkyl or aryl) are required when the organometallic reagent contains Sn or Zr. Such catalysts can optionally be used when the organometallic reagent contains Zn or Al. Other Ni(0) or Pd(0) catalysts can also be employed. When the organometallic reagent contains Sn, and $PdCl_2(dppp)$ is the catalyst, $Al(i-Bu)_2H$ is employed as a co-catalyst to activate the Pd species. Depending on the organo moiety sought to be coupled at the 2- and/or 3-position of the naphthoquinone, the preferred organometallic reagent will comprise Sn, Al, Zr, or Zn in descending order of preference. It has been found, however, that Al-containing organometallics may produce better results when relatively long chain hydrocarbyl substituents are involved at the 2- and/or 3-positions of the naphthoquinone.

It has been found that Lewis acids that do not react with the quinone portion of the reactant can be employed to improve yields when Al or Zn organometallics are used. Useful Lewis acids for this purpose include metal halides such as $ZnX_2$, $MgX_2$ and $AlX_3$.

Typical reaction temperatures are between about 0° C. to 150° C. Reactions with Al organometallics are best at about 20° to 30° C. and those employing Sn organometallics are best at about 60° to 135° C.

The reaction occurs both by addition of naphthoquinone to the organometallic reagent, and by the inverse addition. For $C_{10}$ to $C_{20}$ alkyl zinc reagents, the inverse addition gives higher yields and is preferred. All reactions, except those with Sn reagents, require a relatively moisture-free, inert (nitrogen, argon, etc.) atmosphere.

Solvents can be employed including diethyl ether, 1,2-dimethoxyethane, 2-methoxyethyl ether, 1,4-dioxane and tetrahydrofuran, preferably 1,4-dioxane or tetrahydrofuran. Aliphatic and aromatic hydrocarbons such as hexane and toluene, and halogenated solvents such as carbon tetrachloride and methylene chloride are often deleterious to the reaction and should be avoided.

Quinones can be dissolved in these ether solvents at concentrations of about 1 to 6 weight percent. The organometallic reagent/quinone molar ratio is about 0.2 to 1.2. Catalysts, when used, are present such that the organometallic reagent/catalyst molar ratio is about 20 to 300.

An interesting aspect of this invention concerns the finding that the

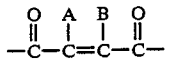

segment of the naphthoquinone starting reactant is subject to cross-coupling addition, at the A and B sites, of the organo moiety from the described organometallic reagents. The process of this invention is characterized by several interrelated advantages. It is single step, versatile in the variety of organometallic reagents and catalysts employed, it produces little or no by-products and is relatively high-yield in certain cases.

Uses for compounds made by the method of this invention are as intermediates to miticides, antibacterials and fungicides. For example, 2-n-dodecyl-3-chloronaphthoquinone is an intermediate to miticides disclosed in U.S. Pat. No. 4,110,473. The compounds, 2-methyl-, 2-ethyl-, 2-propyl-, 2-isopropyl-, and 2-butyl-3-chloronaphthoquinone are, or are intermediates to, antibacterials; Ambrogi, et al., Brit. J. Pharmacol., 40, 871 to 880 (1970). Compounds such as 2-propyl- and 2-butyl-3-chloronaphthoquinone are, or are intermediates to, fungicides; Fieldgate, et al., Pest. Sci., 4, 193 to 200 (1973).

In the following Examples, unless otherwise noted, reactions that did not involve use of Sn were performed in a dry-box atmosphere. These abbreviations are used: THF (tetrahydrofuran); dppp (bis(diphenylphosphino)propane); Cp (cyclopentadienyl); 2,3-DCNQ (2,3-dichloro-1,4-naphthoquinone).

EXAMPLE 1

2-Methyl-3-chloronaphthoquinone

In a 100 mL round bottom flask was added 0.84 g (4.69 mmoles) of $Sn(CH_3)_4$, 1.00 g (4.48 mmoles) of 2,3-DCNQ and 0.02 g (0.026 mmoles) of $PdCl(CH_2Ph)(PPh_3)_2$ in 60 mL of dry 1,4-dioxane. The mixture was refluxed for 1 day and then poured into 50 mL of saturated $NH_4Cl$ solution. The solution was extracted with 3×50 mL of ether; the organic layer was filtered through silica gel and solvent was removed to yield 0.805 g (3.89 mmole, 88.4%) of 2-methyl-3-chloronaphthoquinone. $^1H$ NMR (δ, $CDCl_3$): 8.20 (m, 2H), 7.80 (m, 2H), 2.35 (s, 3H). Other data from similar runs: mp 152° to 154° C. (lit. 152° to 153° C.).

Calculated for $C_{11}H_7ClO_2$: C: 63.94; H: 3.41; Cl: 17.16; Found: C: 63.83, 63.76; H: 3.38, 3.45; Cl: 16.92.

Mass spectrum: Found: $M^+ = 206.0104$; Calculated: $M^+ = 206.0134$. IR ($cm^{-1}$, hexane): 1685s, 1672s, 1602m, 1581w, 1281s.

EXAMPLE 2

2-Ethyl-3-chloronaphthoquinone

To 1.037 g (7.61 mmoles) of $ZnCl_2$ in 20 mL of THF at 0° C. was added 2.40 mL (7.68 mmoles) of 3.2M EtMgBr in ether. The solution was stirred for 0.5 hr at 0° C. and 0.0612 g (0.104 mmole) of $PdCl_2(dppp)$ was added. After stirring for 10 minutes, 1.22 g (5.37 mmoles) of 2,3-DCNQ in THF was added dropwise. The solution was stirred overnight at room temperature. The mixture was poured into 50 mL of NH$_4$Cl solution and extracted with ether. The organic layer was dried over MgSO$_4$, filtered and solvent was removed in vacuo. The residue was chromatographed in silica gel eluted with toluene. A yellow band was collected which yielded 0.71 g of a material which $^1$H NMR in CDCl$_3$ indicated to be a 3.9:1 mixture of 2-ethyl-3-chloronaphthoquinone and 2,2-diethyl-3-chloro-1,4-dihydronaphthoquinone. Recrystallization from hot ethanol gave 0.38 g (1.72 mmoles, 32.1%) of 2-ethyl-3-chloronaphthoquinone. mp: 109° to 110° C. (lit. 111° to 112° C.) $^1$H NMR (δ, CDCl$_3$): 8.15 (m, 2H), 7.85 (m, 2H), 2.85 (q, J=7.5 Hz, 2H), 1.21 (t, J=7.5 Hz, 3H). IR (cm$^{-1}$, hexane): 1690s, 1670s, 1608m, 1582w, 1563w, 1288s.

EXAMPLE 3

2-Ethyl-3-chloronaphthoquinone

To 0.30 g (2.26 mmoles) of AlCl$_3$ in 50 mL of THF was added 2.1 mL of 2.09M EtMgCl in ether (4.40 mmoles). The aluminum reagent was added dropwise to 1.00 g (4.40 mmoles) of 2,3-DCNQ in 100 mL of THF and the mixture was stirred overnight. A homogeneous yellow solution was obtained. Then, 0.300 g (2.21 mmoles) of ZnCl$_2$ was added and the mixture was stirred overnight. A white solid formed; the mixture was poured into 100 mL of NH$_4$Cl solution and extracted with 3×50 mL of ether. The organic layer was dried over MgSO$_4$, filtered and solvent was removed in vacuo. The residue was extracted with hexane, filtered and solvent was removed. The residue was chromatographed in silica gel eluted with toluene to give 0.39 g (1.77 mmole, 40%) of 2-ethyl-3-chloronaphthoquinone.

EXAMPLE 4

2-n-Propyl-3-chloronaphthoquinone

To 1.00 g (4.40 mmoles) of 2,3-DCNQ in 25 mL of THF was added dropwise 0.23 g (1.47 mmoles) of Al(n-propyl)$_3$ in 20 mL of THF. The mixture was stirred overnight and then poured into 100 mL of ice. After warming to room temperature, the solution was extracted with 3×50 mL of ether; the organic layer was dried over MgSO$_4$, filtered and solvent was removed in vacuo. The residue was chromatographed on silica gel eluted with toluene. A yellow band was collected; solvent removal and crystallization from ethanol at −10° C. gave 0.26 g of 2-n-propyl-3-chloronaphthoquinone (1.11 mmoles, 25%). mp: 71° to 73° C. $^1$H NMR (δ, CDCl$_3$): 8.12 (m, 2H), 7.75 (m, 2H), 2.77 (t, J=7.5 Hz, 3H). IR (cm$^{-1}$, hexane): 1692sh, 1684s, 1673s, 1601m, 1582w, 1563w, 1282s.

EXAMPLE 5

2-Isopropyl-3-chloronaphthoquinone

In a 3-neck flask was added 1.00 g (41.67 mmoles) of Mg in 30 mL of ether. To this mixture 5.13 g (41.67 mmoles) of isopropyl bromide in 20 mL of ether at a rate to maintain reflux. After addition, the mixture was refluxed for an additional 0.5 hours. Assuming 100% yield of isopropyl magnesium bromide, a 0.75M solution of Grignard (total volume 55 mL) was obtained.

To 0.60 g (4.41 mmoles) of ZnCl$_2$ in 15 mL of THF in a Schlenk flask at 0° C. was added 6.0 mL (4.5 mmoles) of the above Grignard solution and the mixture was stirred for 0.5 hours. To the zinc reagent was added, at 0° C., 0.030 g (0.051 mmoles) of PdCl$_2$(dppp). After stirring for 10 minutes, 1.00 g (4.40 mmole) of 2,3-DCNQ in 30 mL of THF was added dropwise. The mixture was stirred overnight at room temperature and then poured into 75 mL of NH$_4$Cl solution, extracted with 3×50 mL of ether, dried over MgSO$_4$, filtered, and solvent was removed in vacuo. Column chromatography on silica gel eluted with toluene yielded 0.33 g (1.41 mmoles, 31.9%) of 2-isopropyl-3-chloronaphthoquinone. Recrystallization from hot ethanol gave 0.10 g (9.43 mmole, 9.7% of product, mp: 54° to 56° C. $^1$H NMR (δ, CDCl$_3$): 8.14 (m, 2H), 7.84 (m, 2H), 3.57 (q, J=7 Hz, 1H), 1.38 (d, J=7 Hz, 6H).

EXAMPLE 6

Procedures were the same as in Example 5 except PdCl$_2$(dppp) was not added. After passing the residue through silica gel with toluene, all fractions were combined and solvent was removed. The residue was washed with hexane, the filtrate was concentrated and cooled to −78° C. The formed yellow crystals were filtered to give 0.22 g (0.94 mmoles, 21.3%) of 2-isopropyl-3-chloronaphthoquinone. mp: 57° to 59° C. $^1$H NMR (δ, CDCl$_3$): 8.14 (m, 2H), 7.84 (m, 2H), 3.57 quintet, J=7 Hz, 1H), 1.38 (d, J=7 Hz, 6H). IR (cm$^{-1}$, hexane): 1690s, 1670S, 1599m, 1570m, 1279s.

EXAMPLE 7

2-n-Butyl-3-chloronaphthoquinone

To 0.0487 g (0.083 mmoles) of PdCl$_2$(dppp) in 3 mL of 1,4-dioxane at 0° C. was added 0.10 mL (0.10 mmoles of 1M di-isobutyl aluminum hydride (1M in hexane). After 5 minutes, 0.85 g (3.74 mmole) of 2,3-DCNQ in 25 mL of 1,4-dioxane and 1.31 g (3.77 mmoles) of Sn(n-butyl)$_4$ were added. The solution was refluxed in air for 2 days. Ethanolic KF solution was added and the solution was filtered. To the filtrate was added 50 mL of NH$_4$Cl solution. The mixture was filtered and extracted with 3×50 mL of ether. The ether layer was dried over MgSO$_4$, filtered and solvent was removed in vacuo. Column chromatography of the residue on silica gel eluted with toluene yielded 0.85 g (3.42 mmoles, 91%) of 2-n-butyl-3-chloronaphthoquinone which was shown in a similar run to be recrystallizable from hot ethanol. Data from similar run: mp: 69° to 70° C. $^1$H NMR (δ, CDCl$_3$): 8.17 (m, 2H), 7.86 (m, 2H), 2.85 (t, J=7 Hz, 2H), 1.50 (m, 4H), 1.00 (t, J=4 Hz, 3H). IR (cm$^{-1}$, hexane): 1688s, 1672s, 1601m, 1583w, 1282s.

Analysis: Calculated for C$_{14}$H$_{13}$O$_2$Cl: C: 67.61; H: 5.27; Found: C: 67.95, 67.97; H: 5.43, 5.29.

EXAMPLE 8

2-n-Butyl-3-chloronaphthoquinone

In a 100 mL round bottom flask was added 1.83 g (5.28 mmoles) of Sn(n-butyl)$_4$, 1.00 g (4.40 mmoles) of 2,3-DCNQ and 0.02 g (0.026 mmoles) of PdCl(CH$_2$Ph)(PPh$_3$)$_2$ in 60 mL of 1,4dioxane. The mixture was refluxed in air for 2 days. The cooled solution was poured into 50 mL of NH$_4$Cl solution and extracted with 3×50 mL of ether. Ethanolic KF was added; the solution was filtered and dried over Na$_2$SO$_4$. The solution was filtered, solvent was removed and the residue was chromatographed on silica gel eluted with toluene to give 0.12 g (0.484 mmoles, 11.0% of 2-n-butyl-3-chloronaphthoquinone.

EXAMPLE 9

2-Octyl-3-chloronaphthoquinone $Cp_2ZrCl(octyl)$ was prepared by mixing 1.41 g (5.49 mmoles) of $Cp_2ZrCl(H)$ and 0.71 g (6.34 mmoles) of 1-octene in 10 to 15 mL of toluene for 3 hours. Solvent was removed and 20 mL of THF, 1.00 g (4.40 mmoles) of 2,3-DCNQ and 0.046 g (0.061 mmoles) of $PdCl(CH_2Ph)(PPh_3)_2$ were added. After stirring overnight, solvent was removed; 150 mL of toluene and 200 mL of hexane were added. White precipitate was filtered off; solvent was removed and the residue was extracted with 200 mL of hexane. Filtration, removal of solvent and chromatography on silica gel eluted with toluene yielded 0.53 g (1.74 mmoles, 39.3%) of 2-n-octyl-3-chloronaphthoquinone. This material was recrystallized from hot ethanol. mp: 69° to 70° C. IR (cm$^{-1}$ hexane): 1683s, 1672s, 1600m, 1580w, 1284s.

EXAMPLE 10

2-Octyl-3-chloronaphthoquinone

In a 100 mL round bottom flask was added 1.00 g (4.40 mmoles) of 2,3-DCNQ, 2.50 g (4.37 mmoles) of $Sn(n-C_8H_{17})_4$, 0.02 g (0.026 mmoles) of $PdCl(CH_2Ph)(PPh_3)_2$ and 60 mL of 1,4-dioxane. The mixture was refluxed for 2 days, poured into 50 mL of water, extracted with 3×50 mL of ether, dried over $MgSO_4$, filtered and solvent was removed in vacuo. The residue was chromatographed on silica gel eluted with toluene to give 0.18 g (0.59 mmoles, 13.4%) of 2-n-octyl-3-chloronaphthoquinone. Mass Spectrum: Calculated for $C_{18}H_{21}O_2Cl$: 304.1230. Found: 304.1228. $^1$H NMR ($\delta$, $CDCl_3$): 8.15 (m, 2H), 7.75 (m, 2H), 1.30 (m 12H), 0.85 (m, 3H).

EXAMPLE 11

2-n-Dodecyl-3-chloronaphthoquinone

In a dry nitrogen atmosphere, 2,3-DCNQ (4.54 g, 0.02 mol) was dissolved in 200 mL of dry tetrahydrofuran. To the well-stirred solution was then added anhydrous zinc chloride (5.48 g, 0.04 mol) to yield a pale yellow solution. After cooling the solution to −15° (+15° is sufficient) a solution prepared from dodecyl magnesium bromide (0.028 mole) and aluminum trichloride (1.25 g, 0.0094 mol) in 75 mL of tetrahydrofuran was added over 30 minutes. After stirring for 10 min, the resulting yellow slurry was filtered into 400 mL of water. The product was then extracted into 1L of diethyl ether which was then removed in vacuo to yield a yellow solid. The solid was then extracted with 600 mL of warm hexane and the filtrate was evaporated to yellow solids which were washed with ethanol (50 mL) to yield 5.89 g (81.6%) of 2-n-dodecyl-3-chloronaphthoquinone, mp: 84° to 86° (first crop), and 1.53 g (second crop) which contained 25% of bidodecyl.

EXAMPLE 12

2-n-Dodecyl-3-chloronaphthoquinone

The synthesis was run as in Example 11 but with 9.08 g (0.04 mol) of 2,3-DCNQ, 10.96 g (0.08 mol) of $ZnCl_2$, 0.04 mol of dodecyl magnesium bromide and 1.77 g (0.013 mol) of $AlCl_3$. The addition was conducted at −15° C., then the mixture was stirred for 1.5 h at 20° C. Yield of 2-n-dodecyl-3-chloronaphthoquinone was 9.88 g (68.5%): mp 85° to 86° C.

EXAMPLE 13

2-n-Dodecyl-3-chloronaphthoquinone

The synthesis was run as in Example 11 except that 2.03 g of $AlCl_3$ and 65.98 g of dodecyl MgBr were used. The addition was conducted at 0°, then the mixture was stirred for 1.5 hours at 20° C. This procedure yielded 10.82 g (75%) of 2-n-dodecyl-3-chloronaphthoquinone.

EXAMPLE 14

$Cp_2ZrCl(dodecyl)$ was prepared from 1.12 g of $Cp_2ZrCl(H)$ (4.34 mmoles) and 0.766 g (4.55 mmoles) of 1-dodecene in 25 mL of toluene. After stirring for 2 hours, solvent was removed in vacuo; the residue was dissolved in THF and 0.904 g (3.98 mmoles) of 2,3-DCNQ and 0.030 g (0.040 mmoles) of $PdCl(CH_2Ph)(PPh_3)_2$ were added. After stirring in a dry box environment for 3 days, the solvent was removed in vacuo and the residue was extracted with hexane. The solvent from the extract was removed and the residue was chromatographed on silica gel eluted with toluene to give 0.53 g (1.47 mmol, 36.9%) of 2-n-dodecyl-3-chloronaphthoquinone. Product recrystallized from ethanol had a mp of 84° to 85° C.

EXAMPLE 15

$Cp_2ZrCl(dodecyl)$ was prepared by stirring 0.999 g (3.87 mmoles) of $Cp_2ZrCl(H)$ and 0.778 g (4.62 mmoles) of 1-dodecene in 10 mL of toluene for 4 hours. Solvent was removed and residue dissolved in 50 mL of THF. Added to this solution were 1.01 g (4.40 mmoles) of 2,3-DCNQ and 0.025 g (0.046 mmoles) of $NiCl_2(dppp)$. The mixture was stirred overnight, poured into 50 mL of $NH_4Cl$ solution and extracted with 3×50 mL of hexane. The organic layer was dried over $MgSO_4$, filtered, and solvent was removed in vacuo. Column chromatography on silica gel eluted with toluene gave 0.43 g (1.19 mmoles, 30.7%) of 2-n-dodecyl-13-chloronaphthoquinone.

EXAMPLE 16

To 1.02 g (3.97 mmoles) of $Cp_2ZrCl(H)$ in 20 mL of toluene was added 0.733 g (4.36 mmoles) of 1-dodecene. After stirring overnight, the solvent was removed in vacuo and residue was dissolved in 50 mL of THF; 0.038 g (0.064 mmoles) of $Pd(dppp)Cl_2$ and 0.882 g (3.88 mmoles) of 2,3-DCNQ were added. After stirring overnight, the mixture was poured into 50 mL of $NH_4Cl$ solution and extracted with 3×50 mL of hexane. The organic layer was dried over $MgSO_4$, filtered, and solvent was removed in vacuo. Column chromatography on silica gel eluted with toluene yielded 0.75 g (2.08 mmoles, 53.6%) of 2n-dodecyl-3-chloronaphthoquinone. Recystrallization from ethanol gave 0.33 g (0.92 mmol, 23.6%) of product, mp: 81° to 82° C.

EXAMPLE 17

To 0.0445 g (0.075 mmoles) of $PdCl_2(dppp)$ in 5 mL of 1,4-dioxane at 0° C. was added 0.10 mL (0.10 mmoles) of 1M di-isobutyl aluminum hydride in hexane. After stirring for 10 minutes, 0.73 g (3.22 mmoles) of 2,3-DCNQ in 20 mL of 1,4-dioxane and 2.76 g (3.47 mmoles) of $Sn(dodecyl)_4$ were added at 0° C. The material was slowly warmed to room temperature, refluxed in air for 6 days, then poured into 50 mL of $NH_4Cl$ solution and extracted with 3×50 mL of ether. Ethanolic KF was added and the solution was dried over MgSO$_4$. After filtration, solvent was removed and the residue was chromatographed on silica gel eluted with toluene. The first yellow band was collected, solvent was removed and the residue was washed with ethanol to give 0.29 g (0.80 mmoles, 25.0% of 2-n-dodecyl-3-chloronaphthoquinone.

EXAMPLE 18

To 0.60 g (4.41 mmoles) of ZnCl$_2$ in 50 mL of THF was added 5.32 g of docecylMgBr. The solution was stirred for 10 minutes and transferred to an addition funnel. To a 250 mL round bottom flask was added 1.02 g (4.50 mmoles) of 2,3-DCNQ and 100 mL of THF. The (dodecyl)ZnCl mixture was added dropwise to the 2,3-DCNQ solution. Addition took about 0.5 hours and a green solution was obtained. The mixture was stirred overnight and then poured into 100 mL of NH$_4$Cl solution. The solution was extracted with 3×50 mL of ether to give a clear yellow extract. After drying over MgSO$_4$ and after filtration, the solvent was removed. The yellow residue was washed with about 100 mL of hexane. The yellow solid was collected to give 0.25 g of product, mp: 80° to 82° C. The solvent from the hexane filtrate was removed and the residue was recrystallized with hot ethanol to give 0.64 g of 2-n-dodecyl-3-chloronaphthoquinone, mp: 80° to 82° C. The filtrate was placed in the refrigerator overnight; the solid was filtered and vacuum dried to give an additional 0.075 g of product. Total yield was 0.965 g (2.67 mmoles, 60.6%).

EXAMPLE 19

In a flask, 0.60 g (4.41 mmoles) of ZnCl$_2$ in 50 mL of THF was added 5.30 g of (dodecyl)MgBr (8.34×10$^{-4}$ mole/g, 4.42 mmoles) dropwise. The solution was stirred for 0.5 hours. To an addition funnel was added 1.00 g (4.40 mmoles of 2,3-DCNQ in 100 mL of THF. This solution was added dropwise to the zinc reagent. The addition took longer than 8 hours. The mixture was stirred overnight and then poured into 100 mL of NH$_4$Cl solution. The mixture was extracted with 3×50 mL of ether, dried over MgSO$_4$, and solvent was removed in vacuo. Approximately 100 mL of hexane was added and the yellow solid was removed by filtration. The solvent from the filtrate was removed and the residue was recrystallized from hot ethanol to give 0.12 g (0.33 mmoles, 7.5%) of 2-n-dodecyl-3-chloronaphthoquinone, mp: 78° to 80° C.

EXAMPLE 20

To 1.00 g (3.89 mmoles) of Cp$_2$ZrClH in 10 mL of toluene was added 0.75 g (5.94 mmoles) of 1-dodecene. After stirring overnight, the solvent was removed in vacuo and 10 mL of CH$_2$Cl$_2$ was added. To this solution was added 0.60 g (4.50 mmoles) of AlCl$_3$. After stirring for an additional 0.5 hours, solvent was removed, the residue was dissolved in 20 mL of THF, and 0.900 g (3.96 mmoles) of 2,3-DCNQ in THF was added dropwise. After stirring overnight, the reaction mixture was added to 100 mL of ice and allowed to warm to room temperature. The mixture was extracted with 3×50 mL of ether; the organic layer was dried over MgSO$_4$, filtered, and the solvent was removed in vacuo. The residue was chromatographed on silica gel eluted with toluene to give 0.63 g (1.74 mmoles, 44.9%) of 2-n-dodecyl-3-chloronaphthoquinone, mp: 82° to 84° C.

EXAMPLE 21

To 1.03 g (42.37 mmoles) of Mg in 30 mL of ether was added dropwise 10.65 g (42.73 mmoles) of 1-bromododecane in 40 mL of ether. After addition, the solution was refluxed for an additional 2 hours. Total volume was 70 mL. Assuming 100% conversion, a 0.6M solution of (dodecyl)MgBr was obtained.

To 1.177 g (8.827 mmoles) of AlCl$_3$ in 50 mL of THF at 0° C. was added 16.00 mL of the abowe Grignard solution (assuming 0.6M solution, 9.6 mmoles). The mixture was stirred for 0.5 hours and 2.07 g (9.12 mmoles) of 2,3-DCNQ in 50 ml of THF was added rapidly. The solution was stirred overnight and poured into ice. Extraction was 200 mL of hexane gave an orange-brown solution which was dried over MgSO$_4$. The solution was filtered, solvent was removed and the residue was recrystallized from hot ethanol. Thus, 1.32 g (3.66 mmoles, 41.4%) of 2-dodecyl-3-chloronaphthoquinone was obtained, mp: 84° to 85° C. (lit. 85° to 87° C.). $^1$H NMR ($\delta$, CDCl$_3$): 8.14 (m, 2H), 7.75 (m, 2H), 2.76 (t, J=7.5 Hz, 2H), 1.28 (broad s, 12H), 0.85 (m, 3H). IR (cm$^{-1}$, hexane): 1685s, 1602m, 1583w, 1281s.

EXAMPLE 22

2-Cyclohexyl-3-chloronaphthoquinone

In a 100 mL round bottom flask were added 1.00 g (3.91 mmoles) of Cp$_2$ZrClH, 10 mL of toluene and 0.453 g (5.51 mmoles) of cyclohexene. The mixture was stirred overnight; solvent was removed in vacuo and the residue was dissolved in 25 mL of THF. To this solution was added 0.055 g (0.093 mmoles) of PdCl$_2$(dppp) followed by 0.909 g (4.00 mmoles) of 2,3-DCNQ in 25 mL of THF. The solution was stirred overnight in air. The mixture was poured into 50 mL of ammonium chloride solution, extracted with 3×50 mL of hexane, dried over MgSO$_4$, filtered, and solvent was removed in vacuo. The residue was chromatographed on silica gel eluted with toluene to give 0.34 g (1.24 mmoles, 31.0%) of 2-cyclohexyl-3-chloronaphthoquinone. $^1$H NMR ($\delta$, CDCl$_3$): 8.16 (m, 2H), 7.77 (m, 2H), 3.29 (m, 1H), 2.4-1.1 (m, 10H). Other data from a similar run: mp: 150° to 151° C. (lit: 150° to 152° C.) IR (cm$^{-1}$, hexane): 1682s, 1669s, 1599m, 1565m, 1279s.

EXAMPLE 23

2-Allyl-3-chloronaphthoquinone

Al(allyl)$_2$Cl was prepared from 1.53 g (11.49 mmoles) of AlCl$_3$ and 20 mL of 1.1M allyl magnesium bromide (22 mmoles) in 100 mL of THF. This solution was added dropwise to 5.00 g of 2,3-DCNQ (22.02 mmoles) in 100 mL of THF and the mixture was stirred overnight. The reaction mixture was poured into 100 mL of ice, extracted with 3×50 mL of ether and the organic layer was dried over MgSO$_4$. After filtration, the solvent was removed and the residue was extracted with hexane. The yellow solution was passed through silica gel, eluted with 10% diethyl ether/hexane, and solvent was removed in vacuo. The residue was recrystallized from hot hexane to give 1.10 g (4.73 mmoles, 21%) of 2-allyl-3-chloronaphthoquinone, mp: 69° to 70° C. IR (cm$^{-1}$, hexane): 1682s, 1671s, 1601m, 1580w, 1560w.

EXAMPLE 24

2-(2-butenyl-3-chloronaphthoquinone

To 1.76 g (13.21 mmoles) AlCl$_3$ in 100 mL of THF was added 34.00 g (26.42 mmoles) of 2-butenyl MgBr in THF. This mixture was added dropwise over 55 min to 5.00 g (22.02 mmoles) of 2,3-DCNQ and 6.00 g (44.12 mmoles) of ZnCl$_2$, and the mixture was stirred overnight. The mixture was poured into 100 mL of NH$_4$Cl solution, extracted with 3×100 mL of hexane, filtered, and stripped of solvent. The residue was recrystallized from hot methanol to give 0.38 g (1.54 mmol, 7%) of 2-(2-butenyl)-3-chloronaphthoquinone. $^1$H NMR $\delta$, CDCl$_3$): 8.20 (m, 2H), 7.85 (m, 2H), 5.60 (m, 2H), 3.5 (d, J=6 Hz, 2H), 1.65 (d, J=6 Hz, 3H).

EXAMPLE 25

2-(2-Methyl-2-propenyl)-3-chloronaphthoquinone

To 1.17 g (8.81 mmoles) of AlCl$_3$ in THF was added 41.48 g (26.42 mmoles) of 2-methyl-2-propenyl MgBr in THF. This solution was added to 5.00 g (22.01 mmoles) of 2,3-DCNQ and 7.19 g (52.87 mmoles) of ZnCl$_2$ in THF. The mixture was poured into 100 mL of NH$_4$Cl solution and extracted with 3×100 mL of ether. The organic layer was dried over MgSO$_4$ and solvent was removed by rotary evaporation. The residue was extracted with hexane, filtered, solvent was removed and the residue was recrystallized from hot methanol. Then, 0.73 g (2.96 mmol, 13.4%) of product was obtained from 3 crops. Mass spectrum: calculated for C$_{13}$H$_{14}$O$_2$Cl: 246.0448; found: 246.0452. IR (cm$^{-1}$, hexane): 1687s, 1675m, 1602w, 1288s. mp: 83° to 84° C.

EXAMPLE 26

2-(2-Methyl-2-propenyl)-3-chloronaphthoquinone

To 0.60 g (4.41 mmoles) of ZnCl$_2$ in 50 mL of THF was added 6.93 g (4.41 mmoles) of 2-methyl-2-propenyl MgBr in THF. This mixture was stirred for 30 min and added dropwise over 30 min to 1.00 g (4.40 mmoles) of 2,3-DCNQ in 100 mL of THF. The mixture was stirred overnight, poured into 100 mL of NH$_4$Cl solution, extracted with 3×50 mL of ether, dried over MgSO$_4$, and solvent was removed in vacuo. The residue was extracted with hexane, filtered, and stripped of solvent. The solid was chromatographed on silica gel eluted with toluene to give 0.59 g of impure 2-(2-methyl-2-propenyl)-3-chloronaphthoquinone. $^1$H NMR ($\delta$, CDCl$_3$): 8.30 (m, 2H), 7.85 (m, 2H), 4.90 (m, 1H), 4.80 (m, 1H), 3.63 (s, 2H), 1.95 (s, 3H).

EXAMPLE 27

2-Phenyl-3-chloronaphthoquinone

In a 100 mL round bottom flask was added 1.06 g (4.67 mmoles) of 2,3-DCNQ, 0.027 g (0.036 mmoles of PdCl(CH$_2$Ph) (PPh$_3$)$_2$, 2.00 g (4.68 mmoles) of SnPh$_4$ and 50 mL of THF. The mixture was refluxed for 5 days and then poured into 50 mL of aqueous NH$_4$Cl solution. The mixture was extracted with ether (3×50 mL), dried over Na$_2$SO$_4$ and filtered. Upon removal of solvent, 2.20 g of material was obtained. This was dissolved in ether and ethanolic KF solution was added. After filtration, 100 mL of water was added and the mixture was extracted with ether. The organic layer was dried over Na$_2$SO$_4$, filtered, and vacuum dried to give 95% pure 2-phenyl-3-chloronaphthoquinone (1.07 g, 3.98 mmoles, 85.3%). These data are from a similar run: mp: 111° to 112° C. (lit: 113° C.). $^1$H NMR spectrum ($\delta$, CDCl$_3$): 8.25 (m, 2H), 7.85 (m, 2H), 7.52 (m, 5H). IR (cm$^{-1}$, CHCl$_3$): 16835, 1670s, 1598m, 1573w, 1566w.

EXAMPLE 28

2-Dodecyl-3-chloronaphthoquinone and 2-Dodecyl-3-methoxynaphthoquinone

To 0.20 g (1.50 mmoles) of AlCl$_3$ in 20 mL of THF was added 6.80 g (4.74 mmoles, 0.697 mmoles/g) of dodecyl MgBr. This mixture was added dropwise to 0.789 g (4.49 mmoles) of 2-methoxy-3-chloro-1,4-naphthoquinone and 0.529 g (3.89 mmoles) of ZnCl$_2$ in 50 mL of THF. The mixture was stirred overnight. The green solution was poured into 100 mL of NH$_4$Cl solution, extracted with 3×50 mL of ether, dried over MgSO$_4$, filtered, and solvent was removed. The residue was flash-chromatographed (90% toluene/hexane as eluant) to give 0.075 g (0.021 mmoles, 4.6%) of 2-dodecyl-3-chloronaphthoquinone and 0.246 g (0.55 mmoles, 12.3%) of 2-dodecyl-3-methoxynaphthoquinone. $^1$H NMR ($\delta$, CDCl$_3$): 8.05 (m,2H), 7.65 (m,2H), 4.10 (s,3H), 2.55 (m,2H), 1.3 (br. s,20H), 0.85 (m,3H).

EXAMPLE 29

2-n-Dodecyl-3-bromonaphthoquinone

To 0.155 g (1.16 mmoles) of AlCl$_3$ in 20 mL of THF was added 5.0 g (3.48 mmoles) of dodecyl MgBr (0.697 mmole/g). This mixture was added to 1.00 g (3.17 mmoles) of 2,3-dibromo-1,4-naphthoquinone in 50 mL of THF. A brown solution was obtained. Then, 0.40 g (2.94 mmoles) of ZnCl$_2$ was added and the mixture was stirred overnight. The mixture was poured into 100 mL of NH$_4$Cl solution, extracted with 3×50 mL of ether, dried over MgSO$_4$, filtered, and solvent was removed. The residue was flash-chromatographed (on silica, toluene eluant). Thus, 0.390 g (0.76 mmole, 24%) of 2-n-dodecyl-3-bromo-1,4-naphthoquinone was obtained. mp 98° to 100° C. $^1$H NMR ($\delta$, CDCl$_3$): 8.11 (m,2H), 7.70 (m,2H), 2.90 (m,2H), 1.33 (br. s,20H), 0.90 (m,3H). IR (cm$^{-1}$, CHCl$_3$): 1678s, 1599m, 1579w, 1280s.

EXAMPLE 30

2-Methoxy-3-dodecylnaphthoquinone

To 0.216 g (1.62 mmoles) of AlCl$_3$ in 50 mL of THF was added 7.0 g (0.697 mmoles/g in THF, 4.88 mmoles) of dodecyl MgBr. This mixture was added dropwise to 1.27 g (9.34 mmoles) of ZnCl$_2$ and 1.00 g (4.67 mmoles) of 2,3-dimethoxy-1,4-naphthoquinone in 50 mL of THF. The mixture was stirred overnight, poured into 100 mL of NH$_4$Cl solution, extracted with 3×50 mL of ether, dried over MgSO$_4$, filtered, and solvent was removed by rotary evaporation. The residue was chromatographed on silica gel eluted with toluene. Thus, 0.034 g (0.096 mmoles, 2.1%) of 2-methoxy-3-dodecylnaphthoquinone was obtained.

EXAMPLE 31

To 0.64 g (4.71 mmoles) of ZnCl$_2$ in 50 mL of THF was added 7.0 g (0.697 mmoles/g in THF, 4.88 mmoles) of dodecyl MgBr. This mixture was added dropwise to 1.00 g (4.67 mmoles) of 2,3-dimethoxy-1,4-naphthoquinone in 50 mL of THF. The mixture was stirred overnight and worked up as in Example 30. Thus, 0.223 g (0.626 mmoles, 13.4%) of 2-methoxy-3-dodecyl-1,4-naphthoquinone was obtained, mp: 61° to 63° C. $^1$H NMR ($\delta$, CDCl$_3$): 8.05 (m,2H), 7.65 (m,2H), 4.10 (s,3H), 2.55 (m,2H), 1.30 (br s,20H), 0.85 (m,3H). IR (cm$^{-1}$, KBr): 2950w, 2918s, 2842m, 1666s, 1642m, 1608m, 1589m, 1571w, 1462m, 1338m, 1329m, 1261m, 1255w, 1209m.

EXAMPLE 32

2-Dodecyl-3-chloronaphthoquinone and 2-Dodecyl-3-acetoxynaphthoquinone

First, 0.60 g (4.4 mmoles) of $ZnCl_2$ was dissolved in 20 mL of THF, and 6.30 g (4.39 mmoles, 0.697 mmoles/g) of dodecyl MgBr was added dropwise. After stirring for 15 minutes, this Zn reagent was added dropwise to 1.00 g (4.0 mmoles) of 2-acetoxy-3-chloro-1,4-naphthoquinone in 50 mL of THF. The mixture was stirred overnight and then poured into 100 mL of $NH_4Cl$ solution, extracted with $3 \times 100$ mL of ether, dried over $MgSO_4$, filtered, and solvent was removed. The residue was flash-chromatographed to give 2-dodecyl-3-chloro-1,4-naphthoquinone and 2-dodecyl-3-acetoxy-1,4-naphthoquinone. The dodecylchloro derivative was recrystallized from hot ethanol; 0.217 g (0.603 mmoles, 15%). The dodecylacetoxy derivative was further purified by preparative TLC; 0.079 g (0.21 mmoles, 5%) mp: 49° to 51° C. (lit: 57° to 58° C.). $^1$H NMR ($CDCl_3$, δ): 8.3 (m, 2H), 7.75 (m, 2H), 2.58 (m, 2H), 2.40 (s, 3H), 1.30 (br s, 20H), 0.9 (m, 3H). IR ($CHCl_3$, cm$^{-1}$): 2935s, 2860m, 1775s, 1679s, 1670sh, 1640m, 1600 m.

EXAMPLE 33

To 0.18 g (1.35 mmoles) of $AlCl_3$ in 20 mL of THF was added dropwise 5.90 g (4.11 mmoles, 0.697 mmoles/g) of dodecyl MgBr. This Al reagent was added dropwise to 1.00 g (4.00 mmoles) of 2-acetoxy-3-chloro-1,4-naphthoquinone and 1.09 g (8.0 mmoles) of $ZnCl_2$ in 50 mL of THF. The mixture was stirred overnight and worked up as in Example 32. Thus, 0.239 g (0.66 mmoles, 16.6%) of the dodecylchloro derivative and 0.042 g (0.11 mmoles, 2.7%) of the dodecylacetoxy derivative were obtained.

The embodiments of the invention in which an exclusive property or privilege is claimed are defined as follows:

1. A noncatalytic method for making a 1,4-naphthoquinone derivative comprising reacting a naphthoquinone having the formula

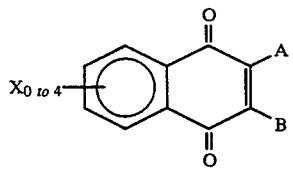

where:
A and B are the same or different and are selected from the group consisting essentially of Cl, Br, I, —OR,

and

X is hydrocarbyl of up to about 20 carbons including straight, branched or cyclic alkyl, aryl, fused-ring aryl, aralkyl, or alkaryl;
R is $C_1$ to $C_5$ alkyl;
$R^1$ is $C_1$ to $C_5$ alkyl, $C_1$ to $C_5$ perfluoroalkyl, or aryl;
$R^2$ is aryl; with an organometallic compound comprising (i) a metal selected from Al and Zn, and (ii) a hydrocarbyl moiety of up to 20 carbon atoms.

2. A method according to claim 1 wherein the organometallic compound is

where $R^4$ is $C_2$ to $C_{20}$ alkyl, cycloalkyl, aryl, $C_7$ to $C_{20}$ aralkyl, or $C_3$ to $C_{20}$ alkenyl; X is —Cl, —Br, —I, or $R^4$, and n=1, 2, or 3.

3. A method according to claim 1 wherein the organometallic compound is

where $R^4$ is $C_2$ to $C_{20}$ alkyl, cycloalkyl, aryl, $C_7$ to $C_{20}$ aralkyl, or $C_3$ to $C_{20}$ alkenyl; and X is —Cl, —Br, —I, or $R^4$.

4. A method according to claim 1 wherein A and B are the same or different and are selected from the group consisting essentially of Cl, Br and I.

5. A method according to claim 4 wherein A and B are each Cl and there are not substitutuents on the left ring of the naphthoquinone.

6. A method according to claim 2 wherein $R^4$ is alkyl of $C_8$ to $C_{20}$.

7. A method according to claim 3 wherein $R^4$ is alkyl of $C_8$ to $C_{20}$.

8. A method according to claim 6 employing a Lewis acid as an additional reactant.

9. A method according to claim 7 employing a Lewis acid as an additional reactant.

10. A method according to claim 5 wherein the organometallic compound is

where $R^4$ is $C_2$ to $C_{20}$ alkyl, cycloalkyl, aryl, $C_7$ to $C_{20}$ aralkyl, or $C_3$ to $C_{20}$ alkenyl; X is —Cl, —Br, —I, or $R^4$, and n=1, 2, or 3.

11. A method according to claim 5 wherein the organometallic compound is

where $R^4$ is $C_2$ to $C_{20}$ alkyl, cycloalkyl, aryl, $C_7$ to $C_{20}$ aralkyl, $C_3$ to $C_{20}$ alkenyl; and X is —Cl, —Br, —I, or $R^4$.

12. A method according to claim 6 wherein A and B are each Cl and there are no substituents on the left ring of the naphthoquinone.

13. A method according to claim 12 employing a Lewis acid as an additional reactant.

14. A method according to claim 7 wherein A and B are each Cl and there are no substituents on the left ring of the naphthoquinone.

15. A method according to claim 14 employing a Lewis acid as an additional reactant.

* * * * *